United States Patent [19]

Trani

[11] Patent Number: 4,632,994
[45] Date of Patent: Dec. 30, 1986

[54] PROCESS FOR DECOMPOSING N-OXIDE DERIVATIVES PRODUCING 5-VINYL-2-PYRROLIDONES

[75] Inventor: Aldo Trani, Milan, Italy

[73] Assignee: Gruppo Lepetit S.p.A., Milan, Italy

[21] Appl. No.: 549,365

[22] Filed: Nov. 4, 1983

[51] Int. Cl.$^4$ .......................................... C07D 207/263
[52] U.S. Cl. .................................................... 548/543
[58] Field of Search .......................................... 548/543

[56] References Cited

PUBLICATIONS

A. C. Cope and E. R. Trumbull, Olefins from Amines: The Hofmann Elimination Reaction and Amine Oxide Pyrolysis in Organic Reactions, vol. XI, Chapter 5, R. E. Krieger Publ. Co., Huntington, New York, 1975.
Cram et al, JACS, 84, pp. 1734–1735 (1962).
Finar, "Organic Chemistry", p. 301, Longman Green and Co., N.Y., N.Y., (1959).
Cope, JACS, 79, p. 4720 (1957).

Primary Examiner—Richard L. Raymond
Assistant Examiner—D. B. Springer
Attorney, Agent, or Firm—Stephen L. Nesbitt

[57] ABSTRACT

New process for preparing olefinic lactams by decomposing the corresponding N,N-dimethyl-N-oxides in a suitable solvent in the presence of a base at a temperature of at least 100° C.

5 Claims, No Drawings

PROCESS FOR DECOMPOSING N-OXIDE DERIVATIVES PRODUCING 5-VINYL-2-PYRROLIDONES

The present invention concerns a process for preparing derivatives of the formula I

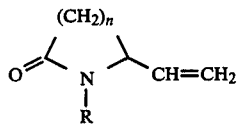

wherein R represents hydrogen, $(C_1-C_4)$alkyl or benzyl and n represents the integer 1, 2, 3 or 4, which comprises:

(a) decomposing a N-oxide derivative of formula II

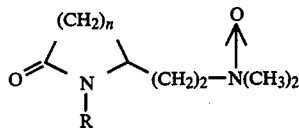

in a suitable organic solvent and preferably in the presence of a base at a temperature of at least 100° C.;

(b) recovering the compound of formula I thus obtained by means of known per se procedures.

The compounds of formula I can be used as intermediates in the preparation of olefinic aminoacids of formula III

$$HOOC-(CH_2)_n-CH(NHR)-CH=CH_2 \quad III$$

which are known to possess CNS-depressant activity as well as other pharmacological activities. These compounds are described for instance in U.S. Pat. Nos. 3,960,927 and 4,039,549.

The transformation of the lactamic derivative of formula I into the compounds of formula III can be accomplished by hydrolyzing the lactamic derivative according to usual procedures.

The starting N-oxides of formula II can be prepared by oxidizing a dimethylamine derivative of formula IV

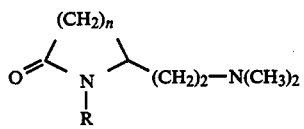

(wherein R and n are as above) by means of hydrogen peroxide.

The dimethylamine derivative of formula IV is in turn prepared by reaction of a cyanide of formula V

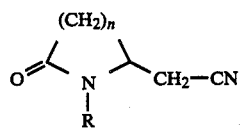

with dimethylamine, in the presence of a hydrogenation catalyst and under a pressure of hydrogen. The reaction temperature is about 40° C. for a hydrogen pressure of about 30 psi.

The preparation of cyanides such as those of formula V are disclosed in J. Org. Chem. 45, 815–818 (1980), which is incorporated herein by reference.

Decomposition reactions of N-oxides of tertiary amines to give olefins and dialkylhydroxylamines are known from A. C. Cope et al., J. Am. Chem. Soc., 71, 3929 (1949). The decomposition described by Cope is a thermal decomposition which occurs at a temperature between 85° C. and 165° C. Generally no particular importance is attached to the solvent used, and in fact the reaction can be carried out without any solvent using a proper apparatus (see A. C. Cope et al. J. Am. Chem. Soc. 79, 4720, (1957), FIG. 1).

Generally this thermal decomposition is not carried out in the presence of a base. In fact the reaction mechanism proposed for this kind of decomposition involves a transition state characterized by "an essentially planar quasi five-membered ring" adduct (see Cope, the cited papers) which, for what is common knowledge in the art, seems to exclude the usefulness of a base in this reaction step. Actually, the skilled man knows that it is not necessary or not useful to add a base to a system characterized by an internal reaction mechanism as the above. The base in fact could compete with the nucleophilic portion of the N-oxide for the electron deficient substrate moiety, and probably change the reaction course.

Surprisingly, it has been found that the decomposition reaction of an N-oxide derivative of formula II in a suitable organic solvent and in the presence of a base give the corresponding olefin of formula I in considerable high yields, yields that are in any case higher than in absence either of the solvent or of the base.

The organic solvent is generally an aprotic solvent, such as a wax or an aromatic solvent having a boiling point higher than 100° C. Representative examples of them are dimethylformamide, xylene, toluene and the like.

Preferred solvents are dimethylformamide and xylene, while the most preferred solvent is xylene. The base can be an organic as well as an inorganic base.

Representative organic bases are tertiary amines, such as dimethylpiperazine while inorganic bases are alkali metal hydroxides or carbonates, such as potassium or sodium hydroxide, potassium or sodium carbonate, and the like. The preferred base is an inorganic base and the most preferred base is potassium carbonate.

The base is generally employed in a molar amount from 1:10 to 3:1 over the N-oxide derivative of formula II. The preferred ratio base/N-oxide being from about 1:1 to about 1:2.

The reaction temperature is generally above 100° C., and preferably between 100° C. and 145° C. The most preferred reaction temperature is between 110° C. and 130° C.

The purification of the reaction product can be carried out by using one of the variety of known purification techniques.

The preferred purification procedure includes an acid washing and a distillation of the crude product of formula I. Generally, however, the compound of formula I obtained according to the process of the invention is pure enough to be submitted to the next reaction step without further purification. In fact, a further advantage of the present process is to yield the main product of formula I substantially free from the impurity represented by the amine of formula IV, which may interfere with the next reaction step or in any case need to be removed from the final product of formula III by means of further purification steps. In many instances this process gives a product wherein the amine impurity is about or less than 1%, and generally is never higher than 10%, while the usual amount of this impurity, when using different processes, is about 10% or more.

The yields in the product of formula I for this reaction step are higher than 75% and in many instances are of 80–85% or more.

Under the conditions of the present process no racemization of optically active compounds is observed. Therefore, starting from an optically active N-oxide of formula II the corresponding olefin of formula I retaining the same optical configuration is obtained.

The following examples illustrate the invention, but are not to be construed as a limitation thereon.

EXAMPLE 1

Preparation of 5-[2-(dimethylaminoethyl)]-2-pyrrolidinone 5-(Cyanomethyl)-2-pyrrolidinone (10 g; 0.08 mole) are dissolved in ethanol (100 ml) and 27% w/v dimethylamine (0.16 mol) in ethanol is added thereto. Then 5% $Pd/Al_2O_3$ is added and the hydrogenation is carried out at a pressure of about 30 psi at a temperature of about 40° C. Stirring is continued until the consumption of hydrogen is ended.

Then the catalyst is recovered by filtration and the filtrate is concentrated. The oily residue is distilled, recovering the fraction having boiling point 130°–135° C. at 1 mmHg.

EXAMPLE 2

Preparation of 5-[2-(dimethylaminoethyl)]-2-pyrrolidinone,N-oxide

5-[2-(dimethylaminoethyl)]-2-pyrrolidinone (7 g; 0.045 mol) are dissolved in water (20 ml) and 36% w/v hydrogen peroxide (5.04 g) is added thereto with stirring at about 20° C. After 2 hours, a further portion of 5.04 g of 36% p/v hydrogen peroxide is added to the reaction mixture and stirring is continued for 24 hours. When the pH of the mixture is about 8.5 or below 8.5, the reaction is considered to be ended. The $H_2O_2$ excess is decomposed by adding powdered platinum. The water is then evaporated under reduced pressure, the residue is taken up with ethanol and the solvent is again evaporated. The white hygroscopic solid obtained is ready for the next reaction step. M.p. 137° C. (acetonitrile).

EXAMPLE 3

Preparation of 5-vinyl-2-pyrrolidinone

5-[2-(dimethylaminoethyl)]-2-pyrrolidinone, N-oxide (11.25 g) is added to xylene (170 ml) and potassium carbonate (3.95 g). Potassium carbonate is preferably powdered $K_2CO_3$ with 80% of particle size distribution less than 300 μm. The temperature of the reaction mixture was kept at about 125° C. for about 2 hours. The suspension is then filtered and the recovered crude product of the title is washed with acids (preferably mineral acids such as 37% hydrochloric acid) adjusting the pH of the mixture to about 3. After distillation at 105°–110° C./1.5 mmHg, a white waxy compound is obtained. Yield 85%. M.p. 21° C. $[\alpha]_D^{20°} = +61°$ (c=2, $H_2O$).

Upon analysis, it is shown to be the compound of the title. Its purity, is such that it can be hydrolyzed without any further purification. In particular, its content in the amine of example 1 is less than 1%.

EXAMPLE 4

Preparation of 5-vinyl-2-pyrrolidinone in the absence of the base catalyst

5-[2-(dimethylaminoethyl)]-2-pyrrolidinone, N-oxide (11.25 g) is added to xylene (170 ml). The temperature of the reaction mixture was kept at about 135° C. for about 2 hours. The suspension is then filtered and the recovered crude product of the title is washed with acids (preferably mineral acids such as 37% hydrochloric acid) adjusting the pH of the mixture to about 3. After distillation at 105°–110° C./1.5 mmHg, a white waxy compound is obtained. Yield. 75%. M.p. 21° C. $[\alpha]_D^{20°} = +61°$ (c=2, $H_2O$).

Upon analysis, it is shown to be the compound of the title having a content in the amine of example 1 of 13.8%.

I claim:

1. In the process of preparing a 5-vinyl-2-pyrrolidinones of the formula

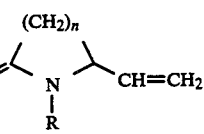

wherein R is hydrogen, a $C_1$–$C_4$ alkyl, or benzyl and n is the integer which comprises decomposing a N-oxide derivative of the formula

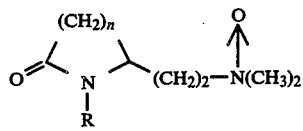

wherein R and n are as defined above at a temperature of at least 100° C., the improvement wherein a suitable organic solvent and an alkali metal hydroxide or carbonate are present.

2. The process of claim 1 wherein the base is potassium carbonate.

3. The process of claim 1 wherein the solvent is xylene.

4. The process of claim 1 wherein the ratio of alkali metal hydroxide or corbonate to the N-oxide is from 1:10 to 3:1.

5. The process of claim 1 wherein the ratio of alkali metal hydroxide or carbonate to the N-oxide is from 1:1 to 1:2.

* * * * *

UNITED STATES PATENT AND TRADEMARK OFFICE
CERTIFICATE OF CORRECTION

PATENT NO. : 4,632,994
DATED : December 30, 1986
INVENTOR(S) : Aldo Trani

It is certified that error appears in the above-identified patent and that said Letters Patent are hereby corrected as shown below:

At column 4, claim 1, line 39, the patent reads "is the integer which" and should read --is the integer 2, which--.

At column 4, claim 1, line 51, the patent reads "and an alkali metal" and should read --and a catalytic amount of alkali metal--.

Signed and Sealed this

Twenty-ninth Day of March, 1988

Attest:

DONALD J. QUIGG

*Attesting Officer*  *Commissioner of Patents and Trademarks*